United States Patent
Lee

(10) Patent No.: US 11,806,169 B2
(45) Date of Patent: Nov. 7, 2023

(54) ELECTRONIC DEVICE FOR INTEGRATING AND PRESENTING PHYSIOLOGICAL DATA BETWEEN MULTIPLE DEVICES AND METHOD THEREOF

(71) Applicant: SAMSUNG ELECTRONICS CO., LTD., Suwon-si (KR)

(72) Inventor: Hongji Lee, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 370 days.

(21) Appl. No.: 17/072,407

(22) Filed: Oct. 16, 2020

(65) Prior Publication Data

US 2021/0113157 A1    Apr. 22, 2021

(30) Foreign Application Priority Data

Oct. 21, 2019  (KR) .................. 10-2019-0130601

(51) Int. Cl.
*A61B 5/00* (2006.01)
*A61B 5/11* (2006.01)

(52) U.S. Cl.
CPC .......... *A61B 5/7271* (2013.01); *A61B 5/0004* (2013.01); *A61B 5/11* (2013.01);
(Continued)

(58) Field of Classification Search
CPC ......... A61B 5/11; A61B 5/7221; A61B 5/742; A61B 5/7271; A61B 5/0004; A61B 5/7246
(Continued)

(56) References Cited

U.S. PATENT DOCUMENTS 6,801,802 B2 * 10/2004 Sitzman ................. A61B 5/363
600/513
9,148,483 B1    9/2015 Molettiere et al.
(Continued)

FOREIGN PATENT DOCUMENTS

| KR | 10-2016-0030807 | 3/2016 |
| KR | 10-2018-0063053 | 6/2018 |
| WO | 2019/055237 | 3/2019 |

OTHER PUBLICATIONS

International Search Report and Written Opinion dated Feb. 15, 2021 in corresponding International Application No. PCT/KR2020/014344.

*Primary Examiner* — Catherine M Voorhees
*Assistant Examiner* — Paroma Mukhopadhyay
(74) *Attorney, Agent, or Firm* — Nixon & Vanderhye P.C.

(57) ABSTRACT

An electronic device is disclosed that includes: communication circuitry, a memory operatively coupled to a processor and storing instructions which, when executed, cause the processor to: receive first physiological data and second physiological data obtained by measuring a physiological state of a user's body, obtain measurement environment data for an environment where each of the first physiological data and the second physiological data is measured, determine validity of each of the first physiological data and the second physiological data based on at least a portion of the measurement environment data, generate integrated data of the first physiological data and the second physiological data based on at least one of comparing the first physiological data with the second physiological data and the measurement environment data, based on the first physiological data and the second physiological data being valid, and control a display to display the integrated data on the display.

16 Claims, 13 Drawing Sheets

(52) U.S. Cl.
CPC .......... *A61B 5/7221* (2013.01); *A61B 5/7246* (2013.01); *A61B 5/742* (2013.01)

(58) Field of Classification Search
USPC ........................................................ 600/301
See application file for complete search history.

(56) References Cited

U.S. PATENT DOCUMENTS

| | | |
|---|---|---|
| 9,369,365 B2 | 6/2016 | Molettiere et al. |
| 9,712,629 B2 | 7/2017 | Molettiere et al. |
| 10,227,063 B2 | 3/2019 | Abreu |
| 10,378,972 B2 | 8/2019 | Silver et al. |
| 2005/0113703 A1* | 5/2005 | Farringdon ............... A61B 5/25 600/509 |
| 2007/0197878 A1 | 8/2007 | Shklarski |
| 2010/0217099 A1* | 8/2010 | LeBoeuf ................ A61B 5/021 600/301 |
| 2012/0165616 A1 | 6/2012 | Geva et al. |
| 2014/0243617 A1* | 8/2014 | LeBoeuf ................ A61B 5/415 600/587 |
| 2015/0094545 A1* | 4/2015 | Russell ................ A61B 5/7282 600/301 |
| 2015/0094914 A1 | 4/2015 | Abreu |
| 2015/0134297 A1 | 5/2015 | Silver et al. |
| 2016/0072690 A1 | 3/2016 | Molettiere et al. |
| 2016/0174903 A1* | 6/2016 | Cutaia ............... A61M 16/0051 128/200.24 |
| 2017/0027521 A1 | 2/2017 | Geva et al. |
| 2019/0076066 A1 | 3/2019 | Ajemba et al. |
| 2019/0076067 A1 | 3/2019 | Ajemba et al. |
| 2019/0076070 A1 | 3/2019 | Nogueira et al. |
| 2019/0216395 A1 | 7/2019 | Geva et al. |
| 2020/0163622 A1 | 5/2020 | Geva et al. |

\* cited by examiner

|   | TIME | DEVICE TYPE | MEASUREMENT LOCATION | HEART RATE | BLOOD PRESSURE | EXERCISE | STRESS | WAVEFORM | MEASUREMENT TECHNOLOGY |
|---|---|---|---|---|---|---|---|---|---|
| 701 — NIBP | ○ | ○ | — | ○ | ○ | — | — | — | — |
| 702 — SMARTPHONE | ○ | ○ | ○ | ○ | ○ | — | △(spot) | ○ | ○ |
| 703 — SMART WATCH | ○ | ○ | ○ | ○ | ○ | ○(continuous) | ○(continuous) | ○ | ○ |
| 704 — EARBUDS | ○ | ○ | ○ | ○ | ○ | ○(continuous) | ○(continuous) | ○ | ○ |

| SBP | DBP | (mmHg) |

125  84

117  76

109  68

Time: 08:30
- Watch (PWA)
- 117/76
- Exercise

· Time difference: 90 min
· BP difference: 0 mmHg
· Device priority: Watch

1102

| SBP | DBP | (mmHg) |

127  85

124  82

Time: 12:28
- Phone (PWA)
- 127/85
- Lunch

Time: 12:30
- NIBP
- 124/82
- Lunch

· Time difference: 2 min
· BP difference: 3 mmHg
· Device priority: NIBP

FIG.11

ELECTRONIC DEVICE FOR INTEGRATING AND PRESENTING PHYSIOLOGICAL DATA BETWEEN MULTIPLE DEVICES AND METHOD THEREOF

CROSS-REFERENCE TO RELATED APPLICATION

This application is based on and claims priority under 35 U.S.C. § 119 to Korean Patent Application No. 10-2019-0130601, filed on Oct. 21, 2019, in the Korean Intellectual Property Office, the disclosure of which is incorporated by reference herein its entirety.

BACKGROUND

1. Field

The disclosure relates to an electronic device for receiving physiological data via multiple devices and integrating and presenting the received physiological data and a method thereof.

2. Description of Related Art

As penetration rates of smartphones and wearable equipment, each of which has excellent performance, have increased, there has been an increase in service where users may have their health care while monitoring their biometric signals in everyday life using their mobile equipment. Particularly, various sensing technologies and services for health-related numerical values, such as blood sugar and blood pressure, which need constant monitoring, have gained popularity.

A non-invasive method of measuring blood pressure may include, for example, the auscultatory method and the oscillometric method. Both the auscultatory method and the oscillometric method may be to measure blood pressure by attaching a cuff to the upper arm of the user, compressing the upper arm of the user with pressure higher than the blood pressure of the systole, and slowly decompressing the upper arm of the user.

Furthermore, there are cuffless methods of estimating blood pressure. They may include a method (hereinafter referred to as "PTT scheme") of using a pulse transit time (PTT) estimating blood pressure using an inverse relationship between blood pressure and the PTT and a pulse wave analysis method (hereinafter referred to as "pulse wave analysis scheme") of analyzing a waveform of a photoplethysmogram (PPG) signal, the mechanism of which is similar to a waveform of blood pressure.

Non-invasive equipment (e.g., a non-invasive blood pressure (NIBP) device) of measuring blood pressure may include, for example, a commercial automatic digital blood pressure monitor of the oscillometric method for determining the blood pressure of the systole and the diastole from a pressure waveform measured by performing compression/decompression using a cuff and cuffless mobile devices for extracting parameters from signals measured from health sensors such as PPG. electrocardiogram (ECG), and pressure sensors and estimating blood pressure.

When an electronic device presents all data at once to present data obtained from two or more devices, readability may be reduced.

Alternatively, when one of two or more devices is selected and presented, because there is an error which occurs in each device due to the characteristics of the device, there may occur a problem of whether to select any value as a reference value.

In addition, when preventing simultaneous measurement due to the problem of presentation, the availability of the device may be reduced.

The above information is presented as background information only to assist with an understanding of the disclosure. No determination has been made, and no assertion is made, as to whether any of the above might be applicable as prior art with regard to the disclosure.

SUMMARY

Embodiments of the disclosure address at least the above-mentioned problems and/or disadvantages and to provide at least the advantages described below. Accordingly, embodiments of the disclosure provide a method and apparatus for determining priorities between data according to selection of valid data and a characteristic of a measurement device and integrating and presenting the data depending on the priorities, when collecting physiological data from a plurality of devices or in various ways in everyday life.

In accordance with an example embodiment of the disclosure, an electronic device is provided. The electronic device may include: a memory operatively connected to a processor and storing instructions which, when executed, cause the processor to: receive first physiological data and/or second physiological data obtained by measuring a physiological state of a user's body via communication circuitry, obtain measurement environment data for an environment where each of the first physiological data and the second physiological data is measured, determine validity of each of the first physiological data and the second physiological data based on at least a portion of the measurement environment data, generate integrated data of the first physiological data and the second physiological data based on at least one comparing the first physiological data with the second physiological data and the measurement environment data-based on the first physiological data and the second physiological data being valid, and control the electronic device to display the integrated data on the display.

In accordance with another example embodiment of the disclosure, a method is provided. The method may include: receiving first physiological data and/or second physiological data obtained by measuring a physiological state of a user's body, obtaining measurement environment data for an environment where each of the first physiological data and the second physiological data is measured, determining validity of each of the first physiological data and the second physiological data based on whether at least a portion of the measurement environment data meets a validity condition, generating integrated data of the first physiological data and the second physiological data based on at least one of comparing the first physiological data with the second physiological data and the measurement environment data-based on the first physiological data and the second physiological data being valid, and displaying the integrated data on a display.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the present disclosure will be more apparent from the following detailed description, taken in conjunction with the accompanying drawings, in which:

FIG. 7 is a diagram illustrating example measurement environment data provided according to a device type according to various embodiments;

FIG. 11 is a diagram illustrating an example blood pressure information message of an electronic device according to various embodiments;

With regard to description of drawings, the same or similar denotations may be used for the same or similar components.

DETAILED DESCRIPTION

Hereinafter, various example embodiments may be described with reference to accompanying drawings. However, it should be understood that this is not intended to limit the disclosure to specific implementation forms and includes various modifications, equivalents, and/or alternatives of embodiments of the disclosure.

In the disclosure, physiological data may refer to data obtained by measuring a physiological state of a user's body. Furthermore, measurement environment data may refer to data about each environment in which the biological data is measured. Furthermore, order information stored in a user account may refer to priority information which is reflected when integrated data is finally generated in the user account.

A measurement device identifier may refer to a data value assigned according to a type of each measurement device to identify each measurement device applied to measure the biological data. Furthermore, a measurement technology identifier may refer to a data value assigned according to each measurement technique to identify each measurement technique applied to measure the biological data.

Figure 1:
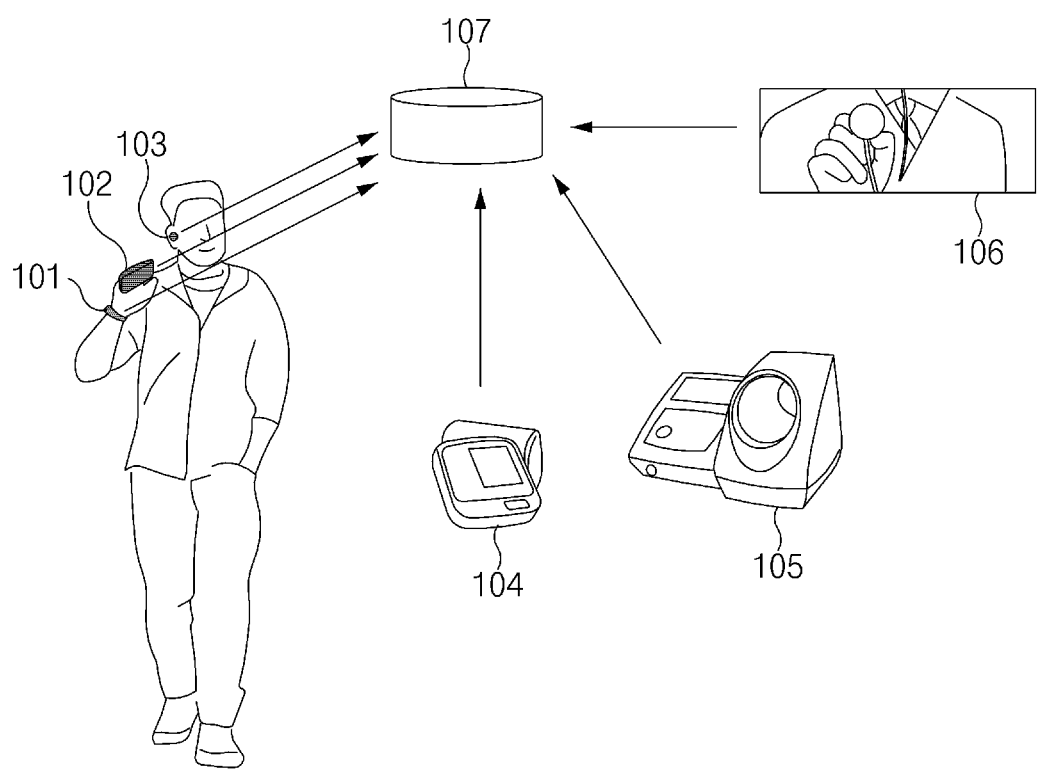
FIG. 1 is a diagram illustrating an example configuration of a system for integrating and presenting physiological data between multiple devices, according to various embodiments.

FIG. 1 is a diagram illustrating an example configuration of a system for integrating and presenting physiological data between multiple devices, according to various embodiments.

According to an embodiment, the disclosure may provide a method for integrating at least two or more biological data collected from a plurality of devices or means and displaying a state most similar to a real state of a user in displaying the integrated biological data to the user by means of an electronic device.

As shown in FIG. 1, a server 107 may receive biological data measured by various devices around the user. For example, the server 107 may receive biological data or the like measured by means of a smart watch 101, a smartphone 102, earbuds 103, an automatic digital blood pressure monitor 104 (e.g., a non-invasive blood pressure (NIBP) device) for home, an automatic digital blood pressure monitor 105 (e.g., an NIBP device) for hospital, or medical checkup 106 at a hospital.

Although not illustrated in FIG. 1, like the server 107, an electronic device may receive biological data measured by various devices around the user.

Each device may measure a biometric state of the user independently, and several devices may measure a biometric state of the user at the same time. In this case, there may be a difference in measurement accuracy and measurement frequency for each device.

For example, the NIBP devices 104 and 105 may transmit biological data with relatively high accuracy to the server 107. On the other hands, a mobile device, such as the smart watch 101, the smartphone 102, or earbuds 103, may be relatively more reduced in accuracy than the NIBP devices 104 and 105, but may measure biological data at high frequency and may transmit the measured biological data to the server 107. Furthermore, the mobile device 101, 102, or 103 may measure various parameters such as a motion state or electrocardiogram (ECG) of the user or a pattern change, thus more accurately measuring whether the user is currently in a stable state. Thus, when generating integrated data, the electronic device may use reference data when determining inaccurate data or data to be excluded.

Furthermore, one device (e.g., the smart watch 101) may measure biological data in various ways depending on a condition using pulse wave analysis or pulse wave velocity analysis using two or more measurement means or schemes.

According to an embodiment, the server 107 or the electronic device (e.g., the smartphone 102) may integrate and present biological data received from biological data measured by means of the smart watch 101, the smartphone 102, the earbuds 103, the NIBP device 104 for home, the NIBP device 105 for hospital, or medical checkup 106 at a hospital and may display the presented biological data on an electronic device (e.g., the smart watch 101 or the smartphone 102) by interworking with, for example, a user account.

Figure 2:
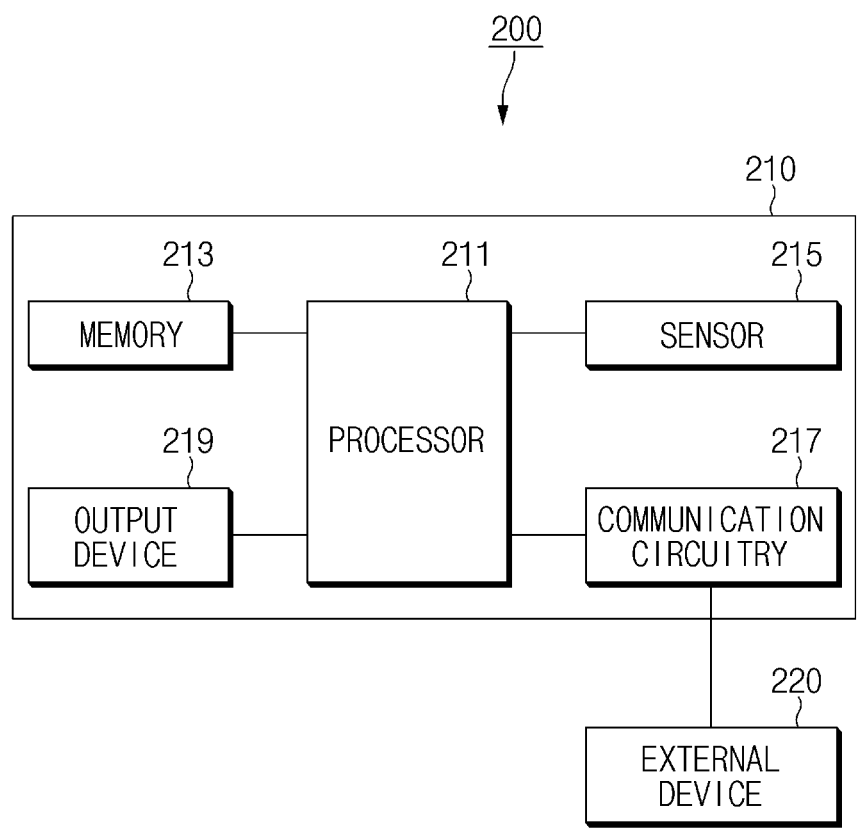
FIG. 2 is a block diagram illustrating an example configuration of an example electronic device according to various embodiments.

FIG. 2 is a block diagram illustrating an example configuration of an electronic device according to various embodiments.

FIG. 2 is a block diagram 200 illustrating an example structure of an electronic device 210 (e.g., an electronic device 1201 of FIG. 12) according to various embodiments.

Figure 12:
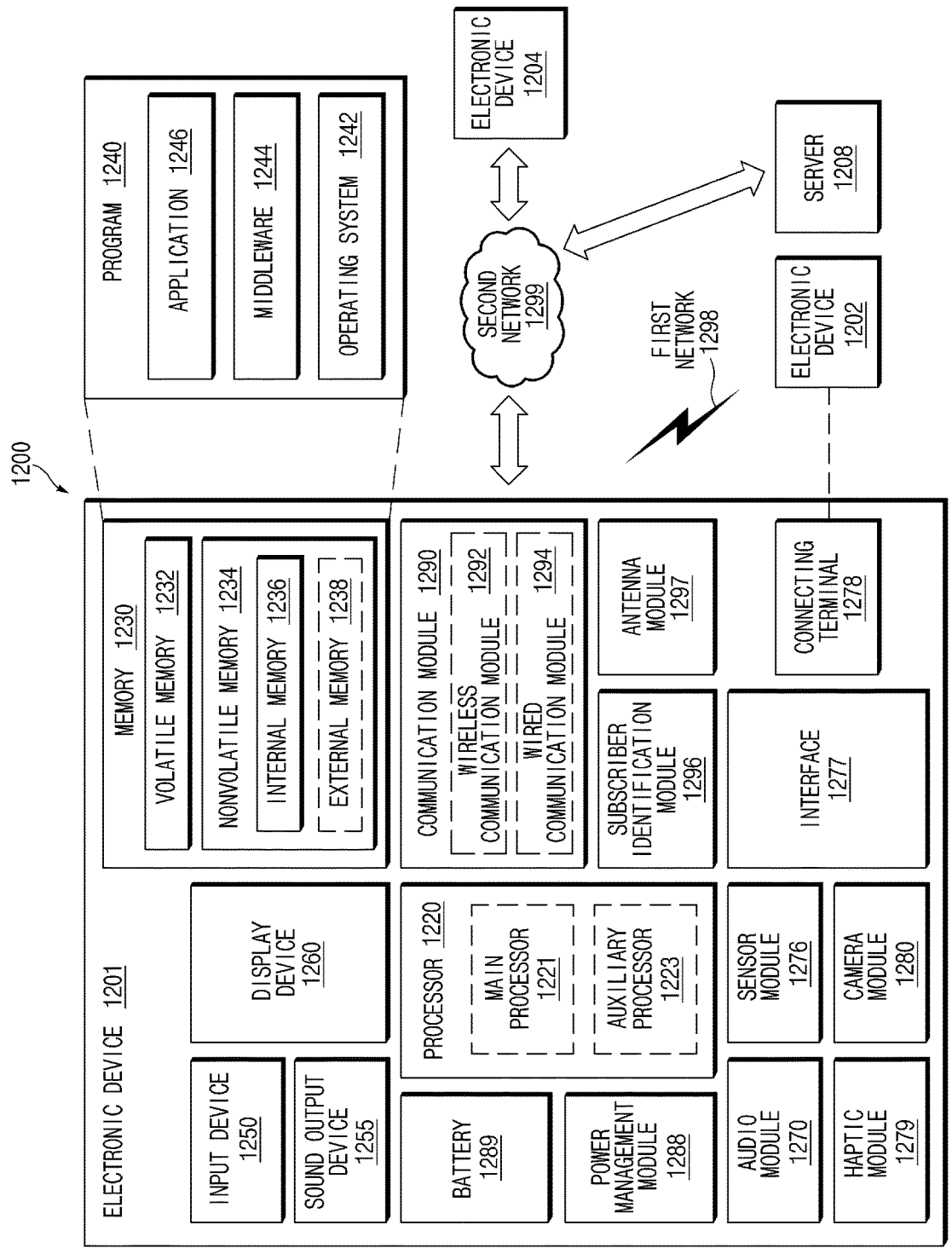
FIG. 12 is a block diagram illustrating an example electronic device in a network environment, according to various embodiments.

According to an embodiment, the electronic device 210 may include a processor (e.g., including processing circuitry) 211 (e.g., a processor 1220 of FIG. 12), a memory 213 (e.g., a memory 1230 of FIG. 12), a sensor 215 (e.g., a sensor module 1276 of FIG. 12), a communication circuitry 217 (e.g., a communication module 1290 of FIG. 12), and an output device (e.g., including output circuitry) 219 (e.g., a display device 1260 or a sound output device 1255 of FIG. 12). Herein, FIG. 2 is to describe an embodiment, and some components thereof may be omitted or changed.

The memory 213 may store instructions which, when executed, cause the processor 211 to process data or control the electronic device 210. In the specification, an operation of the processor 211 or the electronic device 210 may be understood as being performed by executing instructions stored in the memory 213 by the processor 211.

The communication circuitry 217 may include various communication circuitry and transmit and receive a command or data with an external device 220 or another electronic device using, for example, and without limitation, global positioning system (GPS), BLUETOOTH, BLUETOOTH LOW ENERGY (BLE), wireless-fidelity (WI-FI), near field communication (NFC), or the like. The communication circuitry 217 may measure a current location based on the received or detected wireless signal.

The sensor 215 may include various sensors, including, for example, and without limitation, a motion sensor, a photoplethysmogram (PPG) sensor, an electrocardiogram (ECG) sensor, or the like and may measure motion or a biometric signal. The motion sensor may include, for example, and without limitation, an accelerometer, a gyroscope, a barometer, a geomagnetic sensor, or the like and may measure motion of a user.

Furthermore, the electronic device 210 may obtain first physiological data and/or second physiological data obtained by measuring a physiological state of a user body by means of the sensor 215 and may obtain measurement environment data for an environment where each of the first physiological data and the second physiological data is measured.

PPG may refer, for example to a technology used to measure a change in blood volume in the blood vessel by measuring the amount of light transmission using an optical sensor, as the heart repeats its contraction and relaxation, when the blood flow of peripheral blood vessels changes and when the volume of blood vessels changes due to it.

The PPG sensor may include one or more receivers (e.g., photodiodes (PDs)) and one or more emitters (e.g., LEDs). The LED may convert electrical energy into light energy, and the PD may convert light energy into electrical energy. Thus, when light is delivered to user's skin from the LED, some of the light may be absorbed by the skin and the PD may detect the remaining reflected light. The LED may have one or more wavelengths. For example, the LED may have an infrared ray (IR) and visible light (red, blue, green).

When a device embedding the PPG sensor including the PD and the LED is in contact with a portion of the body (e.g., a finger, a wrist, an ear, skin, or the like) and when the contact remains over a certain time, the volume of light detected by the PD may be reduced as blood is increased in blood vessels in the systole and the volume of light detected by the PD may be increased as blood is moved from the diastole. The skin and the veins may fail to have an influence on a change in heartbeat (a DC signal), and an AC signal may be output as the arteries have an influence on a change in heartbeat. This signal may be processed to estimate blood pressure, blood sugar, heartbeat, blood volume, or the like.

ECG may refer, for example, to a technology of measuring voltage generated by the electrical activity of the heart. Muscle cells of the heart may contract and relax due to current which flows from the cardiac conduction system. The ECG sensor may, for example, measure voltage using two or more electrodes and may use a difference between voltages at the two electrodes.

According to an embodiment, the processor 211 may process signals measured by the sensor 215 of the electronic device 210 and may display the processed signal on the output device 219. In this case, the processor 211 may provide the electronic device 210 with feedbacks of sound and vibration together. The processor 211 may control another device or may store data, via the communication circuitry 217. The processor 211 may include at least one or more processors and may be run by being physically divided into a main processor for performing high-performance processing and an auxiliary processor for performing low-power processing. In this case, the PPG sensor or the ECG sensor may be connected to the auxiliary processor to perform 24-hour monitoring.

One processor may perform processing by switching high performance and low power depending on a situation.

Hereinafter, an example operation of the processor 211 will be described in greater detail.

Figure 3:
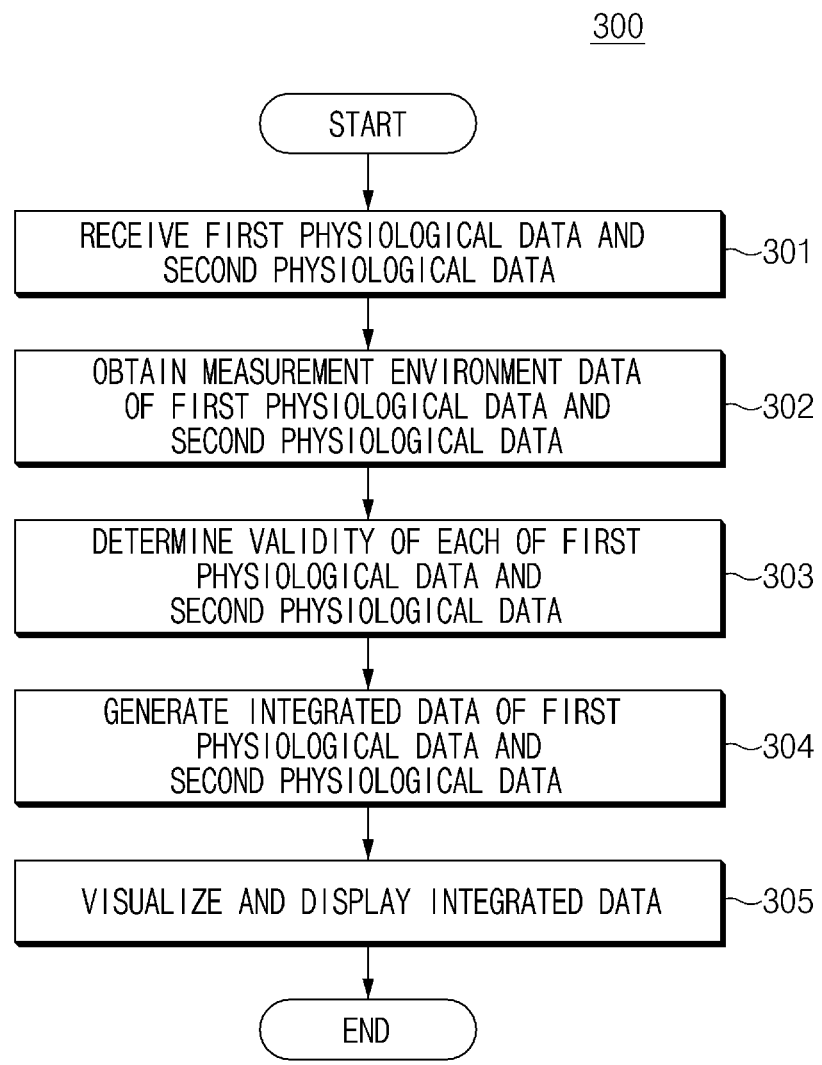
FIG. 3 is a flowchart illustrating an example method for integrating and presenting physiological data between multiple devices of an electronic device, according to various embodiments.

FIG. 3 is a flowchart 300 illustrating an example method for integrating and presenting physiological data between multiple devices of an electronic device, according to various embodiments. According to an embodiment, a process shown in FIG. 3 may, for example, be understood as being performed by executing instructions stored in a memory (e.g., a memory 1230 of FIG. 12) at a processor (e.g., a processor 1220 of FIG. 12) of an electronic device (e.g., an electronic device 1201 of FIG. 12).

In operation 301, the electronic device may receive first physiological data and second physiological data. The first physiological data and the second physiological data may be data measured by the same device or may be data measured by different devices. Physiological data may refer to data obtained by measuring physiological data of a user's body. For example, the physiological data may include, without limitation, blood pressure data measured by a cuff-type digital blood pressure monitor, cuffless-type mobile equipment, or the like at the same time or at intervals of a certain time. In this case, the cuffless-type mobile equipment may refer to all devices including a health sensor, for example, a smartphone (e.g., a smartphone 102 of FIG. 1), a smart watch (e.g., a smart watch 101 of FIG. 1), a fitness band, a patch, earbuds (e.g., earbuds 103 of FIG. 1), or the like.

For another example, the physiological data may be blood pressure data measured according to various measurement technology methods, each of which has different measurement accuracy in one device.

In operation 302, the electronic device may obtain measurement environment data of the first physiological data and the second physiological data.

For example, when the physiological data is measured by means of wearable equipment (e.g., a smartphone or a smart watch), the electronic device may obtain measurement environment data measured using a motion sensor and a heartbeat sensor, which are embedded in the wearable equipment.

When the physiological data is measured by means of an automatic digital blood pressure monitor (e.g., an NIBP device), the electronic device may fail to be easy to obtain the measurement environment data because sensors capable of measuring a state of a user (e.g., whether the user is in a stable state, whether the user is in a stress state, or the like) and a situation of the user are not embedded in the electronic device. In this case, in an embodiment, when physiological data is measured by means of the automatic digital blood pressure monitor (e.g., the NIBP device), the electronic device may obtain measurement environment data measured by a motion senor or the like embedded in wearable equipment interworking with a user account.

In operation 303, the electronic device may determine validity of each of the first physiological data and the second physiological data. The validity may refer to whether the physiological data is data suitable for generating integrated data. The validity may be fluidly varied in determination criteria according to the purpose of generating the integrated data. For example, the determination criteria of the validity may include whether the user is in a stable at the time of measuring the physiological data, whether the physiological data is data measured within a reference time, whether a difference in measured value between the physiological data is within a threshold, or the like. A description will be given in greater detail with reference to FIG. 8 below.

In operation 304, the electronic device may generate integrated data of the first physiological data and the second physiological data. In this case, the electronic device may generate the integrated data using data, the validity of which is recognized in operation 303. For example, when the first physiological data is determined as being valid, but when the second physiological data is not determined as being valid, the first physiological data may be used to generate the integrated data, but the second physiological data may fail to be used to generate the integrated data. In other words, when the second physiological data is determined as data measured when the user exercises between from a previous measurement time to a current measurement time or when the user has a high stress level (when it is not determined that the user is in a stable state), because the second physiological data corresponds to data which is not valid, blood pressure values measured irrespective of a difference in measurement time between two data are recognized as separate data, the electronic device may fail to generate the first physiological data and the integrated data using the second physiological data.

In operation 305, the electronic device may visualize and display the integrated data. A description will be given in greater detail with reference to FIGS. 10 and 11 below.

Figure 4:
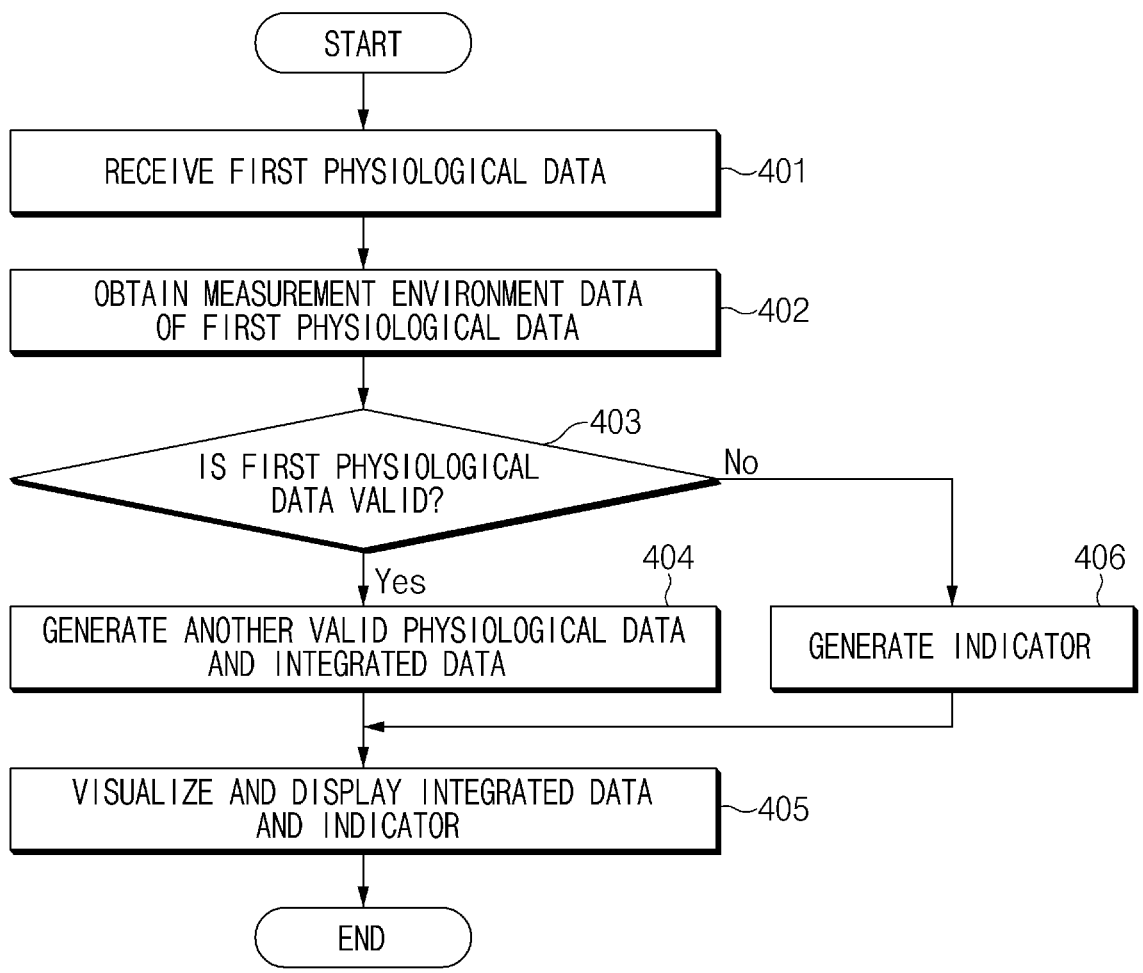
FIG. 4 is a flowchart illustrating an example method for integrating and presenting physiological data between multiple devices of an electronic device, according to various embodiments.

FIG. 4 is a flowchart 400 illustrating an example method for integrating and presenting physiological data between multiple devices of an electronic device, according to various embodiments. According to various embodiments, a process shown in FIG. 4 may be understood as being performed, for example, by executing instructions stored in a memory (e.g., a memory 1230 of FIG. 12) at a processor (e.g., a processor 1220 of FIG. 12) of an electronic device (e.g., an electronic device 1201 of FIG. 12).

In operation 401, the electronic device may receive first physiological data.

In operation 402, the electronic device may obtain measurement environment data of the first physiological data. In this case, the electronic device may determine a user state associated with a time when the first physiological data is measured, based on at least a portion of the measurement environment data.

In operation 403, the electronic device may determine whether the first physiological data is valid. In this case, the electronic device may determine validity based on the user state. When the first physiological data is determined as the valid data based on the user state ("Yes" in operation 403), in operation 404, the electronic device may generate another valid physiological data and integrated data. In this case, the valid data may be integrated according to priority. In operation 405, the integrated data may be visualized and displayed. A description will be given in greater detail below with reference to FIGS. 5, 6, 7, 8, 9 and 10.

Figure 10:
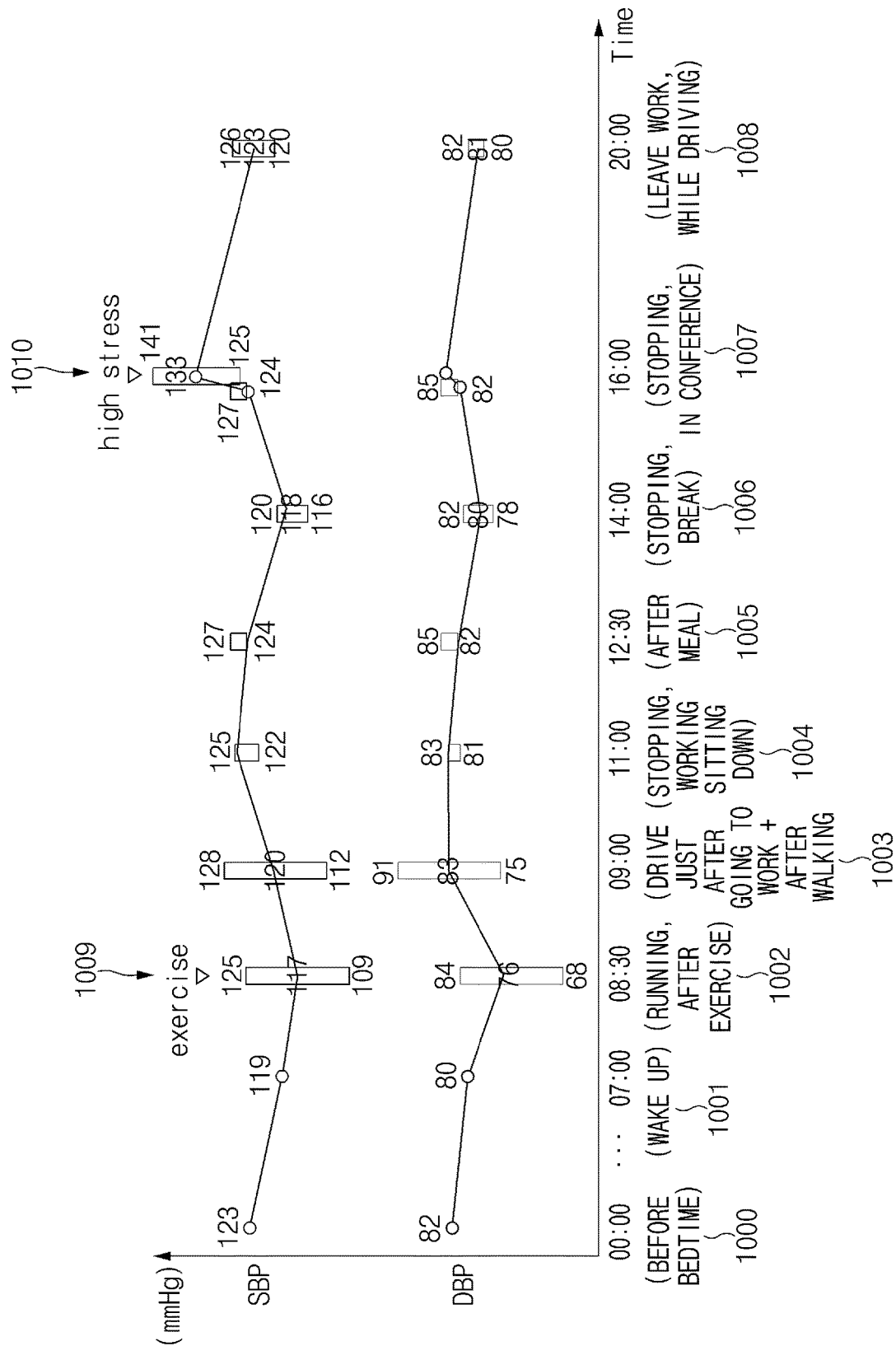
FIG. 10 is a graph illustrating an example of biological data integrated and presented according to a timeline according to various embodiments.

On the other hand, when the first physiological data is determined as invalid data ("No" in operation 403), in operation 406, the electronic device may determine the first physiological data as separate data incapable of being integrated to generate an indicator (e.g., an indicator 1001 or 1002 of FIG. 10). In operation 405, the indicator may be displayed together when the electronic device presents the integrated data. When a user applies an input selecting the displayed indicator, he or she may identify whether the first physiological data is not selected as integrated data for some reason. For example, when the first physiological data is determined as data measured in a stress data, in response to an input of the user to the indicator, the electronic device may display a message indicating that the first physiological data is the data measured in the stress state.

FIG. 4 illustrates an embodiment where an electronic device generates an indicator for invalid data and presents the indicator together with integrated data. This is an example of a method for processing invalid data, and various methods may be used as the method for processing the invalid data. For example, the invalid data may be ignored when the integrated data is generated. A description will be given in greater detail below with reference to FIG. 5.

Figure 5:
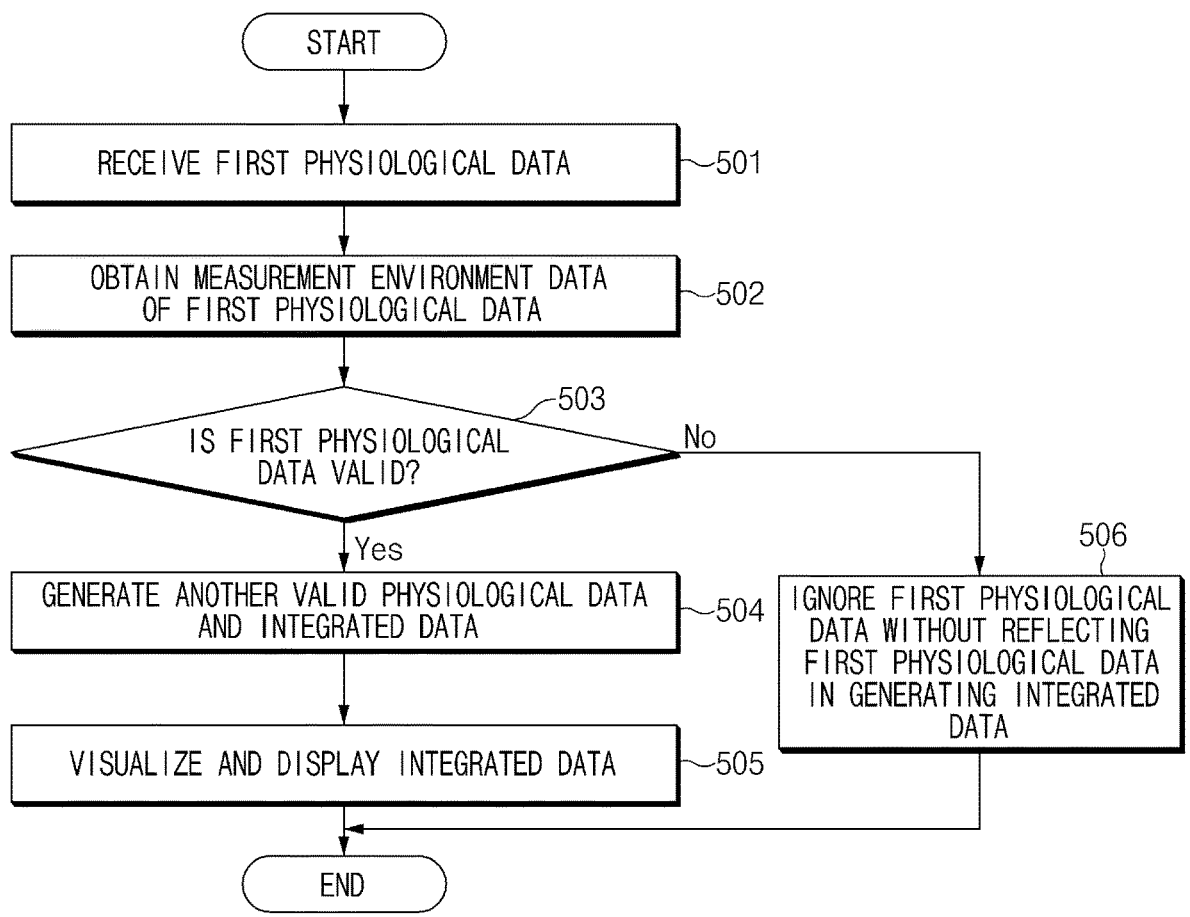
FIG. 5 is a flowchart illustrating an example method for integrating and presenting physiological data between multiple devices of an electronic device, according to various embodiments.

FIG. 5 is a flowchart 500 illustrating an example method for integrating and presenting physiological data between multiple devices of an electronic device, according to various embodiments. According to various embodiments, a process shown in FIG. 5 may, for example, be understood as being performed by executing instructions stored in a memory (e.g., a memory 1230 of FIG. 12) at a processor (e.g., a processor 1220 of FIG. 12) of an electronic device (e.g., an electronic device 1201 of FIG. 12).

In operation 501, the electronic device may receive first physiological data. For example, the electronic device may receive data including a blood pressure value obtained by a blood pressure monitor (e.g., an NIBP device 104 of FIG. 1) connected to the electronic device.

In operation 502, the electronic device may obtain measurement environment data of the first physiological data. For example, the electronic device may determine a user state associated with a time when the first physiological data is measured, based on at least a portion of the measurement environment data.

In operation 503, the electronic device may determine whether the first physiological data is valid. The electronic device may, for example, determine validity based on the user state. When the first physiological data is determined as the valid data based on the user state ("Yes" in operation 503), in operation 504, the electronic device may generate another valid physiological data and integrated data. In this case, the valid data may be integrated according to priority. In operation 505, the integrated data may be visualized (or presented) and displayed. A description will be given in greater detail below with reference to FIGS. 6, 7, 8, 9, 10 and 11.

On the other hand, when the first physiological data is determined as invalid data ("No" in operation 503), in operation 506, the electronic device may determine the first physiological data as separate data incapable of being integrated to ignore the first physiological data without reflecting the first physiological data when generating the integrated data.

For example, when the first physiological data is data where a correction time elapses, the electronic device may determine the first physiological data as invalid data. The electronic device may exclude data where the correction time elapses when generating integrated data and may generate the integrated data using other valid data. When generating the integrated data using invalid data, this is because the electronic device may generate inaccurate integrated data.

For another example, when a device error is detected when measuring the first physiological data, the electronic device may determine the first physiological data as separate data incapable of being integrated to exclude the first physiological data when generating integrated data and may generate the integrated data using other valid data.

In some embodiments, the electronic device may store the excluded data as separate data and may display the data stored as the separate data in response to an input of the user.

According to an embodiment, the process shown in FIG. 5 may be performed using a server. For example, operations 501 to 504 may be performed by the server, and, in operation 505, the server may transmit the presented integrated data to the electronic device and may the electronic device may display the integrated data.

Figure 6:
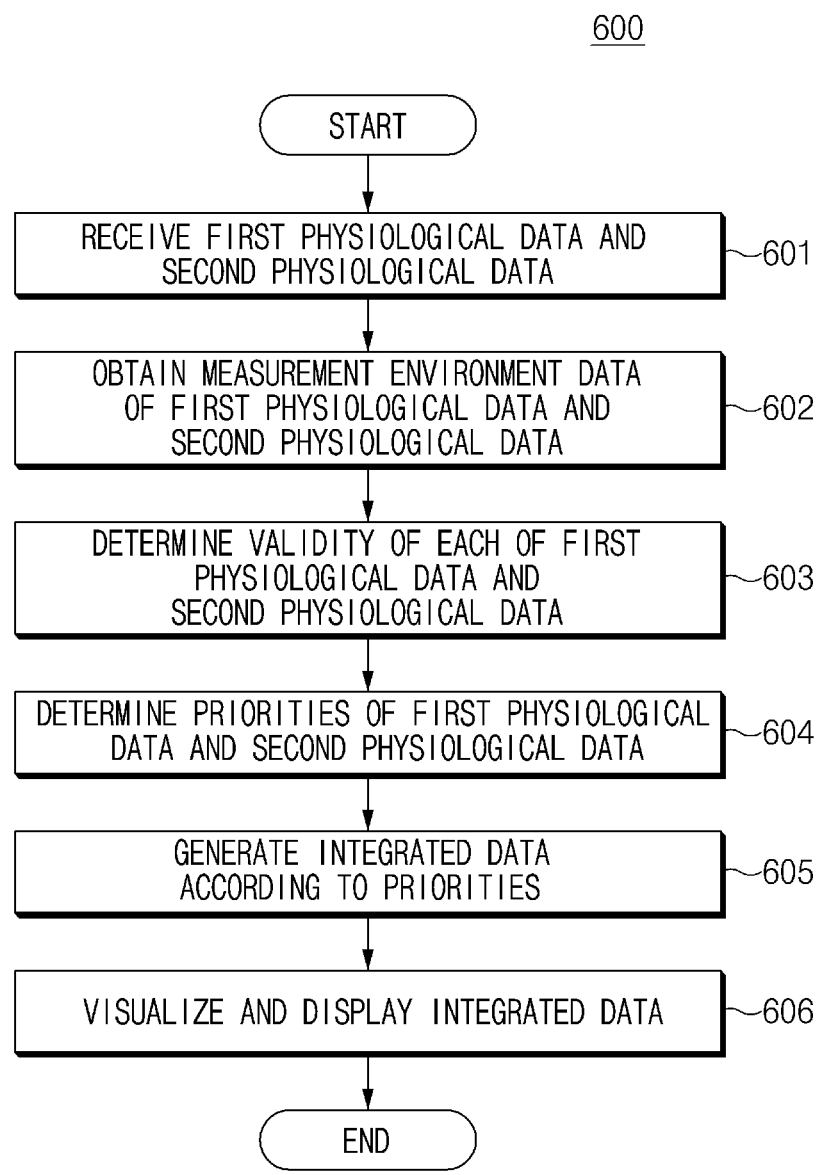
FIG. 6 is a flowchart illustrating an example method for integrating and presenting physiological data between multiple devices of an electronic device, according to various embodiments.

FIG. 6 is a flowchart 600 illustrating an example method for integrating and presenting physiological data between multiple devices of an electronic device, according to various embodiments. According to various embodiments, a process shown in FIG. 6 may, for example, be understood as being performed by executing instructions stored in a memory (e.g., a memory 1230 of FIG. 12) at a processor (e.g., a processor 1220 of FIG. 12) of an electronic device (e.g., an electronic device 1201 of FIG. 12).

In operation 601, the electronic device may receive first physiological data and second physiological data.

In operation 602, the electronic device may obtain measurement environment data of the first physiological data and the second physiological data. In operation 603, the electronic device may determine validity of each of the first physiological data and the second physiological data. Because operations 601 to 603 may be the same as or similar to those described with reference to FIGS. 3 to 4, a detailed description thereof may not be repeated here.

In operation 604, the electronic device may determine priorities of the first physiological data and the second physiological data. In this case, the measurement environment data may include a measurement technology identifier for identifying each measurement technique applied to measure each of the first physiological data and the second physiological data, and the electronic device may determine the priorities based on the measurement technology identifier. The measurement environment data may include a measurement device identifier for identifying each measurement device applied to measure each of the first physiological data and the second physiological data, and the electronic device may determine the priorities based on the measurement device identifier.

In operation 605, the electronic device may generate integrated data according to the priorities. In operation 606, the electronic device may visualize and display the integrated data.

FIG. 7 is a diagram illustrating example measurement environment data provided according to a device type according to various embodiments. As shown in FIG. 7, information included in measurement environment data may vary with a device type of a device which measures physiological data.

As shown in FIG. 7, an electronic device, such as an NIBP device 701, a smartphone 702, a smart watch 703, or earbuds 704, may measure physiological data including measurement environment data, such as a measurement time, a measurement device type, a measurement location, a heart rate, or blood pressure.

Although not illustrated, because the NIBP device 701 should be connected to a phone or a server by BLUETOOTH to deliver information to the phone or the server when measuring blood pressure, a model name of the NIBP device 701 may be included in the measurement environment data. When an NIBP device which does not support BLUETOOTH is used, measurement data obtained after a user captures a screen in an optical character recognition (OCR) scheme using a camera Information, such as a measurement location (e.g., an arm, a finger, a wrist, ears, or the like) or a measurement technology (e.g., an oscillometric method, pulse wave analysis, pulse wave velocity analysis, tonometry, pressure, or the like) measured by the wearable equipment 702 to 704 except for the NIBP device 701, may be included in the measurement environment data. The electronic device may determine whether the measurement devices are the same as each other, whether technologies applied to the measurement scheme are the same as each other, or the like, using information included in such measurement environment data.

When measuring physiological data in a state where a user wears the smart watch 703 or the earbuds 704, the smart watch 703 or the earbuds 704 may include information about an event, which occurs in a time except for the measurement time, and a lapse time (e.g., a sleep time, an exercise time, or the like) in the measurement environment data. When there is a stress measurement record of the user in advance as well as a time when physiological data is measured, the smartphone 702 may include the record in the measurement environment data. The electronic device may determine a state and situation of the user based on the measurement environment data to determine validity of physiological data and may determine priorities between the valid physiological data.

Figure 8:
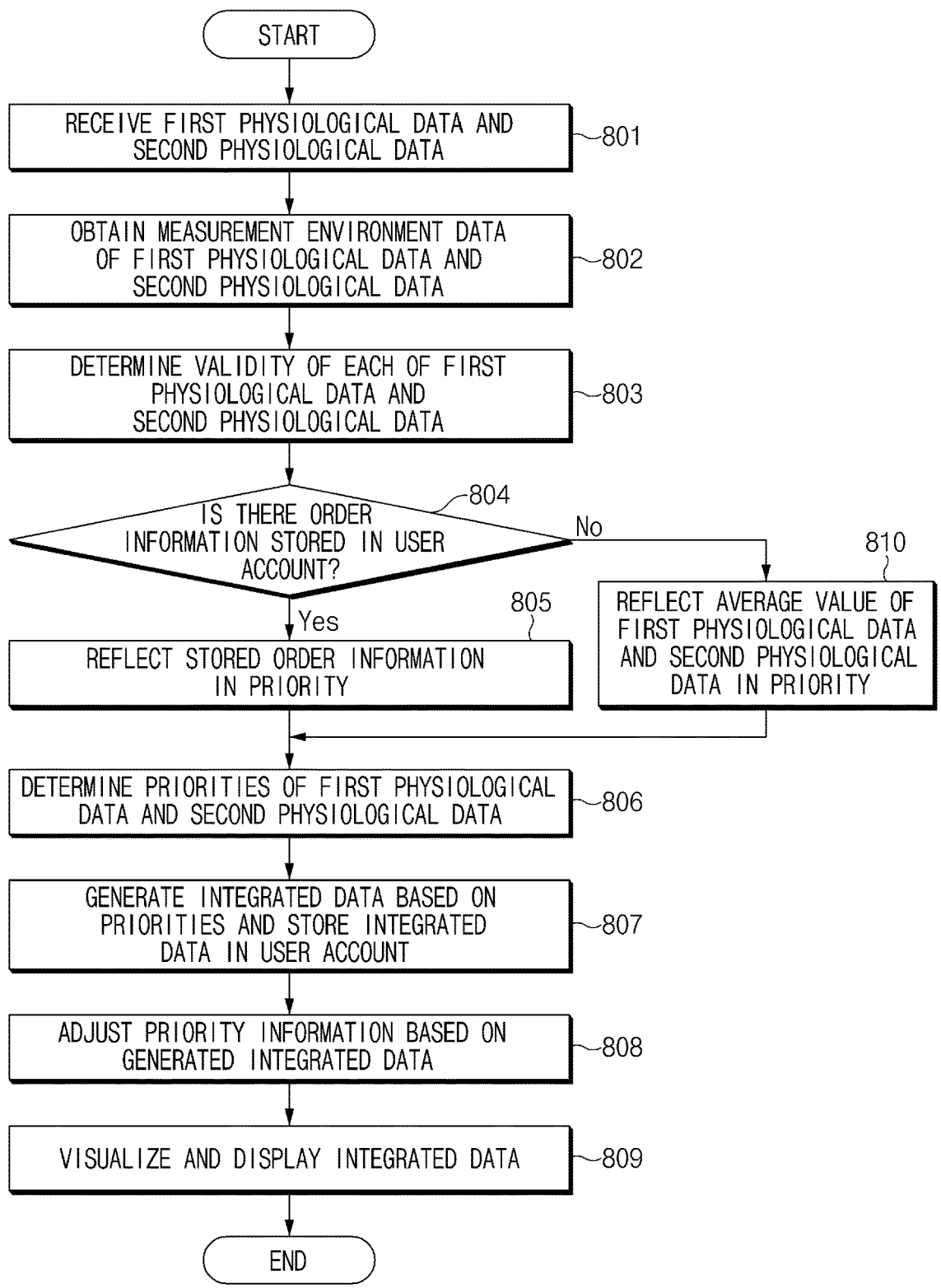
FIG. 8 is a flowchart illustrating an example method for integrating and presenting physiological data between multiple devices of an electronic device, according to various embodiments.

FIG. 8 is a flowchart 800 illustrating an example method for integrating and presenting physiological data between multiple devices of an electronic device, according to various embodiments. According to various embodiments, a process shown in FIG. 8 may, for example, be understood as being performed by executing instructions stored in a memory (e.g., a memory 1230 of FIG. 12) at a processor (e.g., a processor 1220 of FIG. 12) of an electronic device (e.g., an electronic device 1201 of FIG. 12).

In operation 801, the electronic device may receive first physiological data and second physiological data. In operation 802, the electronic device may obtain measurement environment data of the first physiological data and the second physiological data. In operation 803, the electronic device may determine validity of each of the first physiological data and the second physiological data.

In operation 804, the electronic device may determine whether there is order information stored in a user account. In this case, the electronic device may identify the user account interworking with the electronic device. When there is the order information stored in the user account ("Yes" in operation 804), in operation 805, the electronic device may reflect the order information of a user, which is stored in the user account, in priority. In other words, the priority may be applied to suit a characteristic of the user.

When there is no order information stored in the user account ("No" in operation 804), in operation 810, the electronic device may reflect an average value of the first physiological data and the second physiological data in priority. Herein, this is only an example of a method for determining a first priority when there is no order information stored in the user account, and may be performed by another method. For example, the electronic device may determine a rate reflected in priority by a setting of the user.

In operation 806, the electronic device may determine priorities of the first physiological data and the second physiological data. As described above, the priorities may be determined by, for example, considering a measurement device identifier, a measurement technology identifier together.

In operation 807, the electronic device may generate integrated data based on priority and may store the generated integrated data in the user account. In operation 808, the electronic device may adjust priority information based on the generated integrated data. There is an effect capable of adjusting a priority according to a person through the above-mentioned operations.

In operation 809, the electronic device may visualize and display the integrated data.

Figure 9:
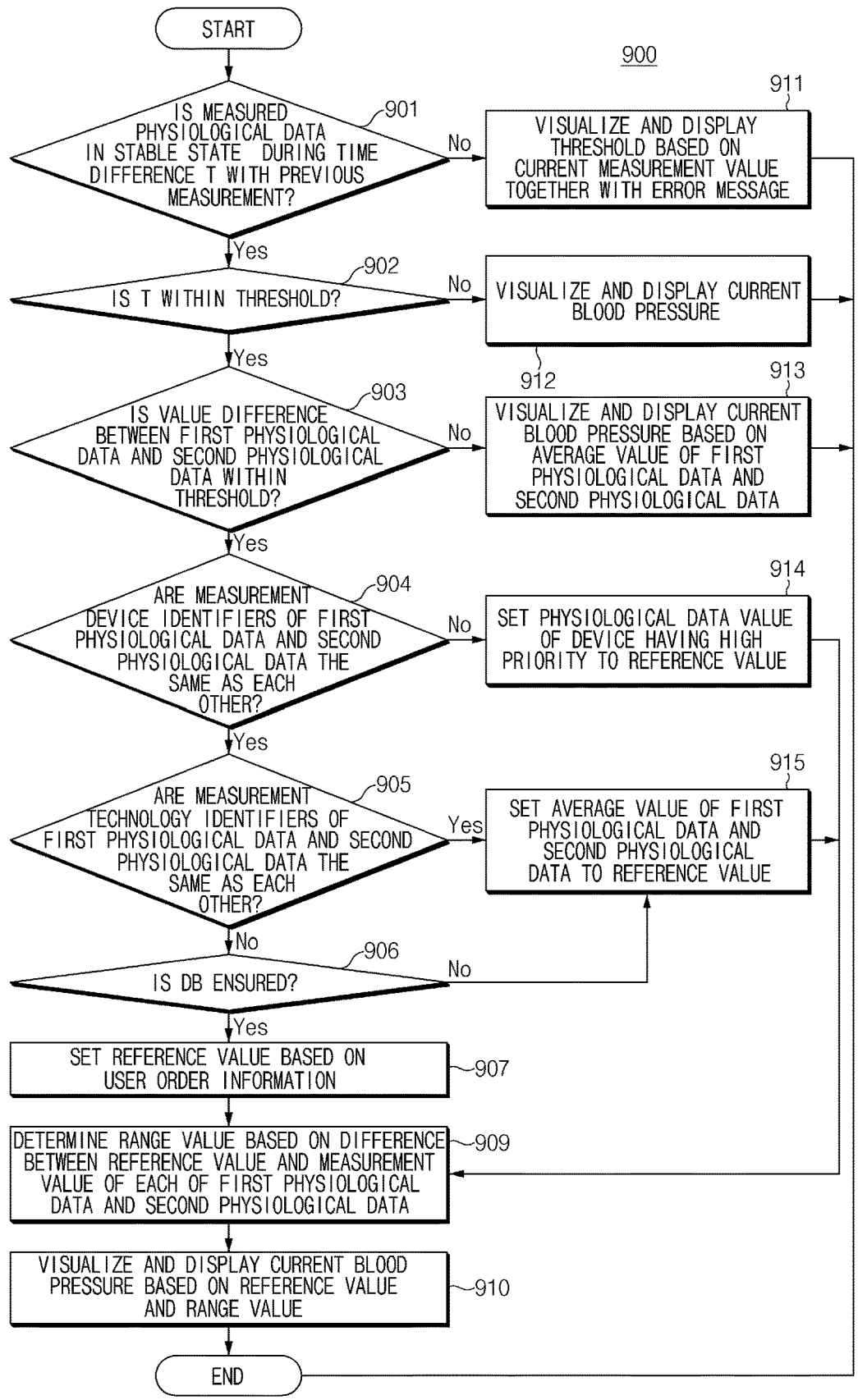
FIG. 9 is a flowchart illustrating an example method for integrating and presenting physiological data between multiple devices of an electronic device, according to various embodiments.

FIG. 9 is a flowchart 900 illustrating an example method for integrating and presenting physiological data between multiple devices of an electronic device, according to various embodiments. According to various embodiments, a process shown in FIG. 9 may, for example, be understood as being performed by executing instructions stored in a memory (e.g., a memory 1230 of FIG. 12) at a processor (e.g., a processor 1220 of FIG. 12) of an electronic device (e.g., an electronic device 1201 of FIG. 12).

In operation 901, the electronic device may determine whether the measured physiological data has a stable state during a time difference T with previous measurement. As described above, information through a motion sensor or a heartbeat sensor may be used to determine that the measured physiological data has the stable state. When it is determined that the measured physiological data does not have the stable state ("No" in operation 901), in operation 911, the electronic device may visualize and display a threshold based on a current measurement value together with an error message.

For example, assuming that the physiological data is blood pressure data, the electronic device may sense a state and situation of a user at the same time as measuring blood pressure of the user. When the user is not in a stable state or when the measurement time is within a certain time after the user exercises, although a time difference between blood pressure data obtained by multiple devices is within 5 minutes, because it is unable to determine the blood pressure data as valid data, the electronic device may fail to integrate the data. Thus, in this case, the electronic device may visualize and display a threshold on the basis of a current measurement value together with an error message.

On the other hand, when it is determined that the measured physiological data has the stable state ("Yes" in operation 901), in operation 902, the electronic device may determine that the time difference T with the previous measurement is within a threshold. Although the physiological data has the stable state, there may be occur large variation in blood pressure over time in the same person. Thus, there is a need for detecting a measurement time difference between measured data and recognizing the measured data as the same data to determine to generate integrated data. In this case, the threshold may be determined according to an international standard for each physiological data.

For example, when the physiological data is blood pressure data, according to a clinical investigation of the ISO 81060-2 standard which is the FDA approval document, a minimum of 3 valid blood pressure data may be obtained for each subject to use the obtained data for data analysis (5.1.1. Number: at least three valid BLOOD PRESSURE DETERMINATIONS shall be taken for each subject). Because it takes about 1 minute to measure blood pressure and because of encouraging the user to measure his or her blood pressure at intervals of 60 seconds, it may be seen that several blood pressure values measured for about 5 minutes in a stable state are valid. Thus, 5 minutes may be set as a threshold. When blood pressure values obtained from multiple devices have motionless, stable state and are values measured within 5 minutes, they may be recognized as being valid to be selected, integrated, and presented.

When it is determined that the time difference T is not within the threshold ("No" in operation 902), in operation 912, the electronic device may visualize and display current blood pressure.

When it is determined that the time difference T is within the threshold ("Yes" in operation 902), in operation 903, the electronic device may determine whether a value difference between first physiological data and second physiological data is within the threshold. In other words, the electronic device may determine validity of data from the difference between the two physiological data to select criteria integrating the selected data. In this case, the threshold for the value difference between the data may be determined according to an international standard for each physiological data. For example, when the physiological data is blood pressure data, according to 5.2.4.1.2.a) Data analysis Criterion 1 of the ISO 81060-2 standard which is the FDA approval document, a blood pressure difference with reference should satisfy an average of 5 mmHg and should satisfy that the standard deviation is within 8 mmHg, such that the developed blood pressure measurement device is approved by the FDA, (the observers' DETERMINATIONS with the REFERENCE SPHYGMOMANOMETER for all subjects shall be within or equal to ±5.0 mmHg (±0.67 kPa), with a standard deviation, no greater than 8.0 mmHg). Thus, only when a difference between two blood pressure values measured irrespective of a type of a blood pressure device is within 8 mmHg, the electronic device may determine that two data are valid.

When it is determined that the value difference is not within the threshold ("No" in operation 903), in operation 913, the electronic device may visualize and display current blood pressure based on an average value of the first physiological data and the second physiological data. On the other hand, when it is determined that the value difference is within the threshold ("Yes" in operation 903), the electronic device may perform operation 904.

In operation 904, the electronic device may determine whether measurement device identifiers of the first physiological data and the second physiological data are the same as each other. When the measurement device identifiers are not the same identifier ("No" in operation 904), in operation 914, the electronic device may set a physiological data value of a device with a high priority to a reference value. For example, when the physiological data is blood pressure data, the accuracy of measuring blood pressure in a device may vary with a characteristic of the device itself. For example, performance may vary with a measurement location (e.g., a finger, a wrist, or ears). For example, because a smart watch type which measures blood pressure on the wrist is more sensitive to a skin-type (a skin color or the amount of skin hairs) than a smartphone type which measures blood pressure on the fingers, it may depend heavily on noise and a user. Thus, the accuracy of estimating blood pressure may be reduced in an order of a finger, ears, and a wrist. Thus, when the measurement device identifier has the smartphone type which measures a finger, it may have a relatively high priority.

When it is determined that the measurement device identifiers are the same as each other ("Yes" in operation 904), in operation 905, the electronic device may determine whether measurement technology identifiers of the first physiological data and the second physiological data are the same as each other. When the measurement technology identifiers are the same each other ("Yes" in operation 905), in operation 915, the electronic device may set an average value of the first physiological data and the second physiological data to a reference value. On the other hand, when the measurement technology identifiers are not the same as each other ("No" in operation 905), in operation 906, the electronic device may determine whether a DB is ensured. When it is determined that the DB is not ensured ("No" in operation 906), operation 915 may be performed. However, when it is determined that the DB is ensured ("Yes" in operation 906), in operation 907, the electronic device may set the reference value based on user order information.

Likewise, assuming that the physiological data is blood pressure data, for data obtained from the same location by means of the same device, accuracy may vary with a measurement technology method. Blood pressure is the pressure of blood vessel. Systolic blood pressure is pressure applied to blood vessels when the heart contracts and pumps blood, and diastolic blood pressure is pressure blood vessels receive when the heart relaxes and receives blood. Thus, it may be seen that an oscillometric method of measuring blood pressure through compression/decompression of a cuff in the same upper arm as a heart height is most accurate among non-invasive blood pressure measurement schemes. There is typically an on-demand automatic digital blood pressure monitor (e.g., an NIBP device).

There are pulse wave analysis and pulse wave velocity analysis as technologies of estimating blood pressure rather than a manner which measures the pressure of blood vessel. The pulse wave analysis is a technology of analyzing the waveform of the pulse wave measured from a PPG single sensor to estimate blood pressure. The pulse wave velocity analysis is a technology of analyzing a time difference between signals measured from a composite sensor, for example, PPG+ECG (pulse arrival time (PAT)) or PPG+BCG (pulse transit time (PTT)). It may be seen that the pulse wave velocity analysis is theoretically more accurate than the pulse wave analysis using only one piece of information, because of using two different mechanisms.

However, because a more accurate measurement technology between the pulse wave velocity analysis and the pulse wave analysis varies for each person, a measurement technology may be differently prioritized for each person by comparing NIBP (reference) measured at the same time or within a certain time with blood pressure data estimated from the pulse wave velocity analysis and the pulse wave analysis. For example, the electronic device may recognize that it is impossible to determine priority until 10 or more DBs are collected to take an average of two blood pressure values obtained in different measurement technology methods in the same device as a criterion, and may set a reference value on the basis of order information in which a priority according to a person is reflected, after the DBs are collected.

When the reference value is set in operation 907, 914, or 915, in operation 909, the electronic device may determine a range value based on a difference between the reference value and a measurement value of each of the first physiological data and the second physiological data. In other words, the electronic device may scope and display other data on the basis of data determined as having a high priority. In operation 910, the electronic device may visualize and display current blood pressure based on the reference value and the range value. A more detailed description will be provided below with reference to FIG. 10.

FIG. 10 is a graph illustrating an example of biological data integrated and visualized according to a timeline according to various embodiments. In detail, FIG. 10 illustrates an example where blood pressure data are integrated and presented according to a 24-hour timeline. Sleep 1000 and 1001, meal 1005, going to work and leaving work 1003 and 1008, exercise 1002, stopping 1004, 1006 and 1007, or the like may be displayed as important events in a timeline. Furthermore, as data has a higher priority, it may be displayed in deeper color. Because two data 1000 and 1001 measured before and after bedtime do not meet 5 minutes which are a condition within a reference time, they may be displayed independently.

Indicators 1009 and 1010 displayed in FIG. 10 will be described in greater detail. It is assumed, by way of non-limiting example, that data is obtained by measuring blood pressure using a smart watch. When it is determined that the data is determined as data measured after exercise from a motion sensor and a heartbeat sensor embedded in the smart watch, the data may be presented in a maximum allowed range of ±8 mmHg on the basis of currently measured blood pressure 117/76 mmHg because a user is not in a stable state. Simultaneously, the data may be displayed with the 'exercise' mark together with the indicator 1009.

It is assumed, by way of non-limiting example, that blood pressure is remeasured when a time difference with previous blood pressure measurement is within 5 minutes. When remeasuring blood pressure, the electronic device may sense a state of a user at the same time as measuring the blood pressure (e.g., the electronic device may receive blood pressure measurement data, motion sensing data, and a heart rate value from a smart watch). As a result of sensing the state of the user, the electronic device may determine the state of the user as a high stress state. When it is determined that the state of the user is the high stress data, because the state of the user is not a stable state, the previously measured blood pressure and the remeasured blood pressure data may fail to be integrated with each other. Thus, the data may be presented in a maximum allowed range of ±8 mmHg on the basis of the remeasured blood pressure data value. Simultaneously, the data may be displayed with the 'high stress' mark together with the indicator 1010.

When the user selects a measurement value on a graph of presenting a change in blood pressure according to a 24-hour timeline, he or she may identify a message in which a current measurement time, a measurement device, a measurement technology method, a blood pressure value, an event, a time difference and blood pressure difference with previous measurement, or priority equipment which is a criterion is recorded. A more detailed description will be provided below with reference to FIG. 11.

FIG. 11 is a diagram illustrating an example blood pressure information message of an electronic device according to various embodiments.

According to an embodiment, when receiving an input selecting an indicator (e.g., an indicator 1009 or 1010 of FIG. 10) or a specific point (e.g., a point 1005 or 1006 of FIG. 10) on the graph, the electronic device may display a message shown in FIG. 11.

The message may be displayed in the form of a pop-up window while the screen shown in FIG. 10 is maintained or may be displayed by being converted from the screen shown in FIG. 10. A description will be given in conjunction with FIG. 10.

When an input selecting the indicator 1009 displayed within the 'exercise' mark of FIG. 10 is received, a left message 1101 of FIG. 11 may be displayed. In the left message 1101, because measured two blood pressure values are data measured in an exercise state within a reference time, they may be presented in a maximum allowed range of ±8 mmHg on the basis of the measured data (117/76 mmHg).

Furthermore, a measurement time, a measurement device, a measurement technology method, a blood pressure value, an event, a time difference and blood pressure difference with previous measurement, priority equipment which is a criterion, or the like may be known using information displayed at a lower end. In detail, it may be seen that the measurement time is 08:30 through a time item above the lower end.

It may also be seen that the measurement device is a smart watch and that the measurement technology method is a PWA scheme through Watch (PWA) displayed below the time item.

Furthermore, the blood pressure value may be known through 117/76, and an exercise state may be known through the indication 'exercise'. When an input selecting a screen to see detailed data for a specific time (e.g., 1005) of FIG. 10 as well as the indicator 1009 or 1010 of FIG. 10 is received, the electronic device may display a message for the detailed data in the same manner as receiving the input selecting the indicator 1009 or 1010. A right message 1102 of FIG. 11 may be displayed, when an input selecting post-dinner (e.g., 1005 of FIG. 10) is received. Because the post-dinner data is data measured in a stable state, it may be displayed in the measured range, rather than the maximum allowed range, unlike the left message 1101. Furthermore, data measured by different devices may be displayed on the right message 1102. As described above, when it is determined that the measured two blood pressure values are measured in a stable state within a reference time, priority may be granted according to a characteristic of a measurement device for data integration. Data (NIBP, 124/82 mmHg) determined as having a high priority may be displayed darker than data (Phone, 127/85 mmHg) measured by another device having a low priority or may be highlighted and displayed.

FIG. 12 is a block diagram illustrating an example electronic device 1201 in a network environment 1200 according to various embodiments. Referring to FIG. 12, the electronic device 1201 may communicate with an electronic device 1202 through a first network 1298 (e.g., a short-range wireless communication network) or may communicate with an electronic device 1204 or a server 1208 through a second network 1299 (e.g., a long-distance wireless communication network) in the network environment 1200. According to an embodiment, the electronic device 1201 may communicate with the electronic device 1204 through the server 1208. According to an embodiment, the electronic device 1201 may include a processor 1220, a memory 1230, an input device 1250, a sound output device 1255, a display device 1260, an audio module 1270, a sensor module 1276, an interface 1277, a haptic module 1279, a camera module 1280, a power management module 1288, a battery 1289, a communication module 1290, a subscriber identification module 1296, or an antenna module 1297. According to some embodiments, at least one (e.g., the display device 1260 or the camera module 1280) among components of the electronic device 1201 may be omitted or one or more other components may be added to the electronic device 1201. According to some embodiments, some of the above components may be implemented with one integrated circuit. For example, the sensor module 1276 (e.g., a fingerprint sensor, an iris sensor, or an illuminance sensor) may be embedded in the display device 1260 (e.g., a display).

The processor 1220 may execute, for example, software (e.g., a program 1240) to control at least one of other components (e.g., a hardware or software component) of the electronic device 1201 connected to the processor 1220 and may process or compute a variety of data. According to an embodiment, as a part of data processing or operation, the processor 1220 may load a command set or data, which is received from other components (e.g., the sensor module 1276 or the communication module 1290), into a volatile memory 1232, may process the command or data loaded into the volatile memory 1232, and may store result data into a nonvolatile memory 1234. According to an embodiment, the processor 1220 may include a main processor 1221 (e.g., a central processing unit or an application processor) and an auxiliary processor 1223 (e.g., a graphic processing device, an image signal processor, a sensor hub processor, or a communication processor), which operates independently from the main processor 1221 or with the main processor 1221. Additionally or alternatively, the auxiliary processor 1223 may use less power than the main processor 1221, or is specified to a designated function. The auxiliary processor 1223 may be implemented separately from the main processor 1221 or as a part thereof.

The auxiliary processor 1223 may control, for example, at least some of functions or states associated with at least one component (e.g., the display device 1260, the sensor module 1276, or the communication module 1290) among the components of the electronic device 1201 instead of the main processor 1221 while the main processor 1221 is in an inactive (e.g., sleep) state or together with the main processor 1221 while the main processor 1221 is in an active (e.g., an application execution) state. According to an embodiment, the auxiliary processor 1223 (e.g., the image signal processor or the communication processor) may be implemented as a part of another component (e.g., the camera module 1280 or the communication module 1290) that is functionally related to the auxiliary processor 1223.

The memory 1230 may store a variety of data used by at least one component (e.g., the processor 1220 or the sensor module 1276) of the electronic device 1201. For example, data may include software (e.g., the program 1240) and input data or output data with respect to commands associated with the software. The memory 1230 may include the volatile memory 1232 or the nonvolatile memory 1234.

The program 1240 may be stored in the memory 1230 as software and may include, for example, an operating system 1242, a middleware 1244, or an application 1246.

The input device 1250 may receive a command or data, which is used for a component (e.g., the processor 1220) of the electronic device 1201, from an outside (e.g., a user) of the electronic device 1201. The input device 1250 may include, for example, a microphone, a mouse, a keyboard, or a digital pen (e.g., a stylus pen).

The sound output device 1255 may output a sound signal to the outside of the electronic device 1201. The sound output device 1255 may include, for example, a speaker or a receiver. The speaker may be used for general purposes, such as multimedia play or recordings play, and the receiver may be used for receiving calls. According to an embodiment, the receiver and the speaker may be either integrally or separately implemented.

The display device 1260 may visually provide information to the outside (e.g., the user) of the electronic device 1201. For example, the display device 1260 may include a display, a hologram device, or a projector and a control circuit for controlling a corresponding device. According to an embodiment, the display device 1260 may include a touch circuitry configured to sense the touch or a sensor circuit (e.g., a pressure sensor) for measuring an intensity of pressure on the touch.

The audio module 1270 may convert a sound and an electrical signal in dual directions. According to an embodiment, the audio module 1270 may obtain the sound through the input device 1250 or may output the sound through the sound output device 1255 or an external electronic device (e.g., the electronic device 1202) (e.g., a speaker or a headphone) directly or wirelessly connected to the electronic device 1201.

The sensor module 1276 may generate an electrical signal or a data value corresponding to an operating state (e.g., power or temperature) inside or an environmental state (e.g., a user state) outside the electronic device 1201. According to an embodiment, the sensor module 1276 may include, for example, a gesture sensor, a gyro sensor, a barometric pressure sensor, a magnetic sensor, an acceleration sensor, a grip sensor, a proximity sensor, a color sensor, an infrared sensor, a biometric sensor, a temperature sensor, a humidity sensor, or an illuminance sensor.

The interface 1277 may support one or more designated protocols to allow the electronic device 1201 to connect directly or wirelessly to the external electronic device (e.g., the electronic device 1202). According to an embodiment, the interface 1277 may include, for example, an HDMI (high-definition multimedia interface), a USB (universal serial bus) interface, an SD card interface, or an audio interface.

A connecting terminal 1278 may include a connector that physically connects the electronic device 1201 to the external electronic device (e.g., the electronic device 1202). According to an embodiment, the connecting terminal 1278 may include, for example, an HDMI connector, a USB connector, an SD card connector, or an audio connector (e.g., a headphone connector).

The haptic module 1279 may convert an electrical signal to a mechanical stimulation (e.g., vibration or movement) or an electrical stimulation perceived by the user through tactile or kinesthetic sensations. According to an embodiment, the haptic module 1279 may include, for example, a motor, a piezoelectric element, or an electric stimulator.

The camera module 1280 may shoot a still image or a video image. According to an embodiment, the camera module 1280 may include, for example, at least one or more lenses, image sensors, image signal processors, or flashes.

The power management module 1288 may manage power supplied to the electronic device 1201. According to an embodiment, the power management module 1288 may be implemented as at least a part of a power management integrated circuit (PMIC).

The battery 1289 may supply power to at least one component of the electronic device 1201. According to an embodiment, the battery 1289 may include, for example, a non-rechargeable (primary) battery, a rechargeable (secondary) battery, or a fuel cell.

The communication module 1290 may establish a direct (e.g., wired) or wireless communication channel between the electronic device 1201 and the external electronic device (e.g., the electronic device 1202, the electronic device 1204, or the server 1208) and support communication execution through the established communication channel. The communication module 1290 may include at least one communication processor operating independently from the processor 1220 (e.g., the application processor) and supporting the direct (e.g., wired) communication or the wireless communication. According to an embodiment, the communication module 1290 may include a wireless communication module 1292 (e.g., a cellular communication module, a short-range wireless communication module, or a GNSS (global navigation satellite system) communication module) or a wired communication module 1294 (e.g., an LAN (local area network) communication module or a power line communication module). The corresponding communication module among the above communication modules may communicate with the external electronic device 1204 through the first network 1298 (e.g., the short-range communication network such as a BLUETOOTH, a WIFI DIRECT, or an IRDA (infrared data association)) or the second network 1299 (e.g., the long-distance wireless communication network such as a cellular network, an internet, or a computer network (e.g., LAN or WAN)). The above-mentioned various communication modules may be implemented into one component (e.g., a single chip) or into separate components (e.g., chips), respectively. The wireless communication module 1292 may identify and authenticate the electronic device 1201 using user information (e.g., international mobile subscriber identity (IMSI)) stored in the subscriber identification module 1296 in the communication network, such as the first network 1298 or the second network 1299.

The antenna module 1297 may transmit or receive a signal or power to or from the outside (e.g., the external electronic device) of the electronic device 1201. According to an embodiment, the antenna module 1297 may include an antenna including a radiating element include a conductive material or a conductive pattern formed in or on a substrate (e.g., PCB). According to an embodiment, the antenna module 1297 may include a plurality of antennas. In such a case, at least one antenna appropriate for a communication scheme used in the communication network, such as the first network 1298 or the second network 1299, may be selected, for example, by the communication module 1290 from the plurality of antennas. The signal or the power may then be transmitted or received between the communication module 1290 and the external electronic device via the selected at least one antenna. According to an embodiment, another component (e.g., a radio frequency integrated circuit (RFIC)) other than the radiating element may be additionally formed as part of the antenna module 1297.

At least some components among the components may be connected to each other through a communication method (e.g., a bus, a GPIO (general purpose input and output), an SPI (serial peripheral interface), or an MIPI (mobile industry processor interface)) used between peripheral devices to exchange signals (e.g., a command or data) with each other.

According to an embodiment, the command or data may be transmitted or received between the electronic device 1201 and the external electronic device 1204 through the server 1208 connected to the second network 1299. Each of the external electronic devices 1202 and 1204 may be the same or different types as or from the electronic device 1201. According to an embodiment, all or some of the operations performed by the electronic device 1201 may be performed by one or more external electronic devices among the external electronic devices 1202, 1204, or 1208. For example, when the electronic device 1201 performs some functions or services automatically or by request from a user or another device, the electronic device 1201 may request one or more external electronic devices to perform at least some of the functions related to the functions or services, in addition to or instead of performing the functions or services by itself. The one or more external electronic devices receiving the request may carry out at least a part of the requested function or service or the additional function or service associated with the request and transmit the execution result to the electronic device 1201. The electronic device 1201 may provide the result as is or after additional processing as at least a part of the response to the request. To this end, for example, a cloud computing, distributed computing, or client-server computing technology may be used.

Figure 13:
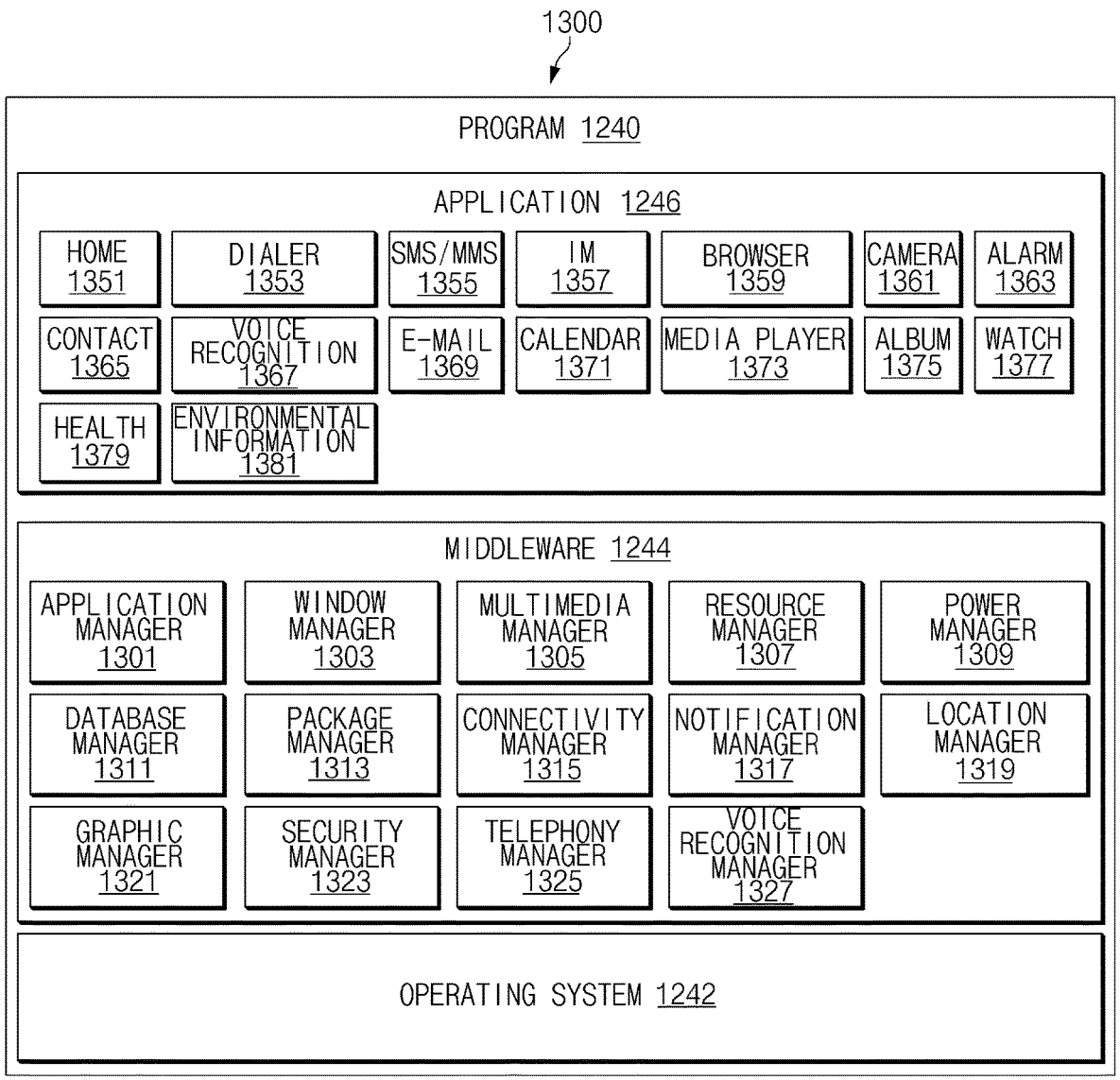
FIG. 13 is a block diagram illustrating an example program according to various embodiments.

FIG. 13 is a block diagram 1300 illustrating an example program 1240 according to various embodiments. According to an embodiment, a program 1240 may include an operating system 1242 for controlling one or more resources of an electronic device 1201, middleware 1244, and an application 1246 executable by the operating system 1242. The operating system 1242 may include, for example, Android, iOS™, Windows™, Symbian™, Tizen™, or Bada™. For example, at least a portion of the program 1240 may be preloaded on the electronic device 1201 when the electronic device 1201 is manufactured or may be downloaded and updated from an external electronic device (e.g., an electronic device 1202 or 1204 or a server 1208 of FIG. 12) when the electronic device 1201 is used by a user.

The operating system 1242 may control to manage (e.g., assign or collect) one or more system resources (e.g., a process, a memory, or a power supply) of the electronic device 1201. Additionally or alternatively, the operating system 1242 may include one or more driver programs for driving another hardware device of the electronic device 1201, for example, an input device 1250, a sound output device 1255, a display device 1260, an audio module 1270, a sensor module 1276, an interface 1277, a haptic module 1279, a camera module 1280, a power management module 1288, a battery 1289, a communication module 1290, a subscriber identification module 1296, or an antenna module 1297 of FIG. 12.

The middleware 1244 may provide the application 1246 with various functions such that functions or information provided from one or more resources of the electronic device 1201 may be used by the application 1246. The middleware 1244 may include, for example, an application manager 1301, a window manager 1303, a multimedia manager 1305, a resource manager 1307, a power manager 1309, a database manager 1311, a package manager 1313, a connectivity manager 1315, a notification manager 1317, a location manager 1319, a graphic manager 1321, a security manager 1323, a telephony manager 1325, or a voice recognition manager 1327.

The application manager 1301 may manage, for example, a life cycle of the application 1246. The window manager 1303 may manage, for example, one or more graphic user interface (GUI) resources used on a screen. The multimedia manager 1305 may identify, for example, one or more formats necessary for playing media files and may encode or decode a corresponding media file among the media files using a codec suitable for the format selected among the one or more formats. The resource manager 1307 may manage, for example, a source code of the application 1246 or a memory space of a memory 1230 of FIG. 12. The power manager 1309 may manage, for example, capacity, temperature, or power of the battery 1289 and may determine or provide related information necessary for an operation of the electronic device 1201 using the corresponding information among the capacity, the temperature, or the power of the battery 1289. According to an embodiment, the power manager 1309 may interwork with a basic input/output system (BIOS) (not shown) of the electronic device 1201.

The database manager 1311 may generate, search, or modify, for example, a database to be used by the application 1246. The package manager 1313 may manage to install or update, for example, an application distributed in the form of a package file. The connectivity manager 1315 may manage, for example, a wireless connection or a direct connection between the electronic device 1201 and the external electronic device. The notification manager 1317 may provide, for example, a function for notifying a user that a specified event (e.g., an incoming call, a message, or an alarm) occurs. The location manager 1319 may manage, for example, location information of the electronic device 1201. The graphic manager 1321 may manage, for example, one or more graphic effects to be provided to the user or may manage a UI associated with the graphic effects.

The security manager 1323 may provide, for example, system security or user authentication. The telephony manager 1325 may manage, for example, a voice or video call function provided by the electronic device 1201. The voice recognition manager 1327 may transmit, for example, voice data of the user to the server 1208 and may receive a command corresponding to a function to be performed in the electronic device 1201 based at least in part on the voice data or text data converted based at least in part on the voice data from the server 1208. According to an embodiment, the middleware 1344 may dynamically fail to include some of the existing components or may further include new components. According to an embodiment, at least a portion of the middleware 1244 may be included as a portion of the operating system 1242 or may be implemented as separate software different from the operating system 1242.

The application 1246 may include, for example, a home application 1351, a dialer application 1353, an SMS/MMS application 1355, an instant message (IM) application 1357, a browser application 1359, a camera application 1361, an alarm application 1363, a contact application 1365, a voice recognition application 1367, an e-mail application 1369, a calendar application 1371, a media player application 1373, an album application 1375, a watch application 1377, a health application 1379 (e.g., an application for measuring biometric information such as an exercise quantity or blood sugar), or an environmental information application 1381 (e.g., an application for measuring information about barometric pressure, humidity, or temperature). According to an embodiment, the application 1246 may further include an information exchanging application (not shown) capable of supporting information exchange between the electronic device 1201 and the external electronic device. The information exchanging application may include, for example, a notification relay application configured to transmit specified information (e.g., a call, a message, or an alarm) to the external electronic device or a device management application configured to manage the external electronic device. For example, the notification relay application may transmit notification information corresponding to a specified event (e.g., mail reception) which occurs in another application (e.g., the e-mail application 1369) of the electronic device 1201 to the external electronic device. Additionally or alternatively, the notification relay application may receive notification information from the external electronic device and may provide a user of the electronic device 1201 with the received notification information.

The device management application may control, for example, a power (e.g., turn-on/turn-off of the power) of the external electronic device which communicates with the electronic device 1201 and a power of each of some components (e.g., the display device 1260 or the camera module 1280) of the electronic device 1201 or may control a function (e.g., brightness, resolution, or focus) of each of some components (e.g., the display device 1260 or the camera module 1280) the electronic device 1201. Additionally or alternatively, the device management application may support the installation, deletion, or update of an application running on the external electronic device.

The electronic device according to various embodiments disclosed in the disclosure may be various types of devices. The electronic device may include, for example, a portable communication device (e.g., a smartphone), a computer device, a portable multimedia device, a mobile medical appliance, a camera, a wearable device, a home appliance, or the like. The electronic device according to an embodiment of the disclosure should not be limited to the above-mentioned devices.

It should be understood that various embodiments of the disclosure and terms used in the embodiments do not intend to limit technical features disclosed in the disclosure to the particular embodiment disclosed herein; rather, the disclosure should be understood to include various modifications, equivalents, or alternatives of embodiments of the disclosure. With regard to description of drawings, similar or related components may be assigned with similar reference numerals. As used herein, singular forms of noun corresponding to an item may include one or more items unless the context clearly indicates otherwise. In the disclosure disclosed herein, each of the expressions "A or B", "at least one of A and B", "at least one of A or B", "A, B, or C", "one or more of A, B, and C", or "one or more of A, B, or C", and the like used herein may include any and all combinations of one or more of the associated listed items. The expressions, such as "a first", "a second", "the first", or "the second", may be used merely for the purpose of distinguishing a component from the other components, but do not limit the corresponding components in other aspect (e.g., the importance or the order). It is to be understood that if an element (e.g., a first element) is referred to, with or without the term "operatively" or "communicatively", as "coupled with," "coupled to," "connected with," or "connected to" another element (e.g., a second element), the element may be coupled with the other element directly (e.g., wiredly), wirelessly, or via a third element.

The term "module" used in the disclosure may include a unit implemented in hardware, software, or firmware or any combination thereof, and may be interchangeably used with the terms "logic", "logical block", "part" and "circuit". The "module" may be a minimum unit of an integrated part or may be a part thereof. The "module" may be a minimum unit for performing one or more functions or a part thereof. For example, according to an embodiment, the "module" may include an application-specific integrated circuit (ASIC).

Various embodiments of the disclosure may be implemented by software (e.g., the program 1240) including an instruction stored in a machine-readable storage medium (e.g., an internal memory 1236 or an external memory 1238) readable by a machine (e.g., the electronic device 1201). For example, the processor (e.g., the processor 1220) of a machine (e.g., the electronic device 1201) may call the instruction from the machine-readable storage medium and execute the instructions thus called. Accordingly, the machine may perform at least one function based on the called at least one instruction. The one or more instructions may include a code made by a compiler or a code executable by an interpreter. The machine-readable storage medium may be provided in the form of non-transitory storage medium. Here, the "non-transitory", storage medium is tangible, but may not include a signal (e.g., an electromagnetic wave). The term "non-transitory" does not differentiate a case where the data is permanently stored in the storage medium from a case where the data is temporally stored in the storage medium.

According to an embodiment, the method according to various embodiments disclosed in the disclosure may be provided as a part of a computer program product. The computer program product may be traded between a seller and a buyer as a product. The computer program product may be distributed in the form of machine-readable storage medium (e.g., a compact disc read only memory (CD-ROM)) or may be directly distributed (e.g., download or upload) online through an application store (e.g., a Play Store™) or between two user devices (e.g., the smartphones). In the case of online distribution, at least a portion of the computer program product may be temporarily stored or generated in a machine-readable storage medium such as a memory of a manufacturer's server, an application store's server, or a relay server.

According to various embodiments, each component (e.g., the module or the program) of the above-described components may include one or plural entities. According to various embodiments, at least one or more components of the above components or operations may be omitted, or one or more components or operations may be added. Alternatively or additionally, some components (e.g., the module or the program) may be integrated in one component. In this case, the integrated component may perform the same or similar functions performed by each corresponding components prior to the integration. According to various embodiments, operations performed by a module, a programming, or other components may be executed sequentially, in parallel, repeatedly, or in a heuristic method, or at least some operations may be executed in different sequences, omitted, or other operations may be added.

According to various example embodiments disclosed in the disclosure, the method for integrating and presenting a plurality of physiological data to have high readability and the electronic device therefor may be provided.

According to various example embodiments disclosed in the disclosure, the method for determining validity and priority of data and presenting optimal integrated data similar to a health status of the user when integrating the plurality of physiological data and the electronic device therefor may be provided.

In addition, various effects ascertained directly or indirectly through the disclosure may be provided.

While the disclosure has been illustrated and described with reference to various example embodiments, it will be understood that the various example embodiments are intended to be illustrative, not limiting. It will be further understood by those skilled in the art that various changes in form and detail may be made without departing from the true spirit and full scope of the disclosure, including the appended claims and their equivalents.

What is claimed is:

1. An electronic device, comprising:
communication circuitry configured to receive data from at least one external device and/or transmit data to the at least one external device;
a display;
a processor operatively connected with the communication circuitry and the display; and
a memory operatively connected with the processor,
wherein the memory stores instructions which, when executed, cause the processor to:
receive, via the communication circuitry, first physiological data and second physiological data obtained by measuring a physiological state of a body of a user, wherein the first physiological data is from a first external device and the second physiological data is from a second external device;
obtain first sensing data associated with the first external device and with a time during which the first physiological data is measured by the first external device, and second sensing data associated with the second external device and with a time during which the second physiological data is measured by the second external device;
determine, based on the first sensing data and the second sensing data, a user state indicating whether the user is in a stable state or in an unstable state during a period of time the first physiological data is measured by the first external device and/or the second physiological data is measured by the second external device;
based on the user determined to be in the stable state during the period, generate integrated data of the first physiological data and the second physiological data based on comparing the first physiological data with the second physiological data;
wherein generating the integrated data includes,
based on a difference between the first physiological data and the second physiological data not being within a threshold value, generate the integrated data based on an average value of the first physiological data and the second physiological data; and
based on the difference between the first physiological data and the second physiological data being within the threshold value, set a value of the first physiological data or the second physiological data to a reference value based on a priority for each of the first physiological data and the second physiological data, determine a range value for the reference value based on a difference between the reference value and a measurement value of each of the first physiological data and the second physiological data, and generate the integrated data based on the reference value and the range value; and
control the display to display the integrated data changing with time.

2. The electronic device of claim 1, wherein the first sensing data and the second sensing data include motion data obtained by measuring motion of the user.

3. The electronic device of claim 1, wherein the instructions, when executed, cause the processor to:

determine the priority for each of the first physiological data and the second physiological data based on the first sensing data and the second sensing data; and
generate the integrated data based on the priorities.

4. The electronic device of claim 3, wherein the first sensing data and the second sensing data include a measurement technology identifier identifying each measurement technique applied to measure each of the first physiological data and the second physiological data, and
wherein the instructions, when executed, cause the processor to:
determine the priorities based on the measurement technology identifier.

5. The electronic device of claim 3, wherein the first sensing data and the second sensing data include a measurement device identifier identifying each measurement device applied to measure each of the first physiological data and the second physiological data, and
wherein the instructions, when executed, cause the processor to:
determine the priorities based on the measurement device identifier.

6. The electronic device of claim 3, wherein the instructions, when executed, cause the processor to:
identify a user account of the user interworking with the electronic device and determine the priorities based on order information of the user, the order information being stored in the user account.

7. The electronic device of claim 6, wherein the instructions, when executed, cause the processor to:
store the generated integrated data in the user account and adjust the order information of the user based on the stored integrated data.

8. The electronic device of claim 1, wherein the instructions, when executed, cause the processor to:
when the user is determined to be in the unstable state during the period, display data excluding at least one of the first physiological data and the second physiological data; and
further control the display to display an indicator indicating that the displayed data does not include at least one of the first physiological data and the second physiological data, based on at least one of the first physiological data and the second physiological data not being included in the displayed data.

9. A method performed in an electronic device, the method comprising:
receiving first physiological data and second physiological data obtained by measuring a physiological state of a body of a user, wherein the first physiological data is obtained from a first external device and the second physiological data is obtained from a second external device;
obtaining first sensing data associated with the first external device and with a time during which the first physiological data is measured by the first external device, and second sensing data associated with the second external device and with a time during which the second physiological data is measured by the second external device;
determining, based on the first sensing data and the second sensing data, a user state indicating whether the user is in a stable state or in an unstable state during a period of time the first physiological data is measured by the first external device and/or the second physiological data is measured by the second external device;

when the user is determined to be in the stable state during the period, generating integrated data of the first physiological data and the second physiological data based on comparing the first physiological data with the second physiological data;

wherein generating the integrated data includes, based on a difference between the first physiological data and the second physiological data not being within a threshold value, generate the integrated data based on an average value of the first physiological data and the second physiological data; and based on the difference between the first physiological data and the second physiological data being within the threshold value, set a value of the first physiological data or the second physiological data to a reference value based on a priority for each of the first physiological data and the second physiological data, determine a range value for the reference value based on a difference between the reference value and a measurement value of each of the first physiological data and the second physiological data, and generate the integrated data based on the reference value and the range value; and displaying the integrated data changing with time.

10. The method of claim 9, wherein the first sensing data and the second sensing data include motion data obtained by measuring motion of the user.

11. The method of claim 9, further comprising:

determining the priority for each of the first physiological data and the second physiological data based on the first sensing data and the second sensing data; and generating the integrated data based on the priorities.

12. The method of claim 11, wherein the first sensing data and the second sensing data include a measurement technology identifier identifying each measurement technique applied to measure each of the first physiological data and the second physiological data, further comprising:

determining the priorities based on the measurement technology identifier.

13. The method of claim 11, wherein the first sensing data and the second sensing data include a measurement device identifier identifying each measurement device applied to measure each of the first physiological data and the second physiological data, and further comprising:

determining the priorities based on the measurement device identifier.

14. The method of claim 11, further comprising:

identifying a user account of the user interworking with the electronic device and determining the priorities based on order information of the user, the order information being stored in the user account.

15. The method of claim 14, further comprising:

storing the generated integrated data in the user account and adjusting the order information of the user based on the stored integrated data.

16. The method of claim 9, further comprising:

when the user is determined to be in the unstable state during the period, displaying data excluding at least one of the first physiological data and the second physiological data; and further displaying an indicator indicating that the displayed data does not include at least one of the first physiological data and the second physiological data, based on at least one of the first physiological data and the second physiological data not being included in the displayed data.

* * * * *